US009051268B2

(12) United States Patent
Yoshida et al.

(10) Patent No.: US 9,051,268 B2
(45) Date of Patent: Jun. 9, 2015

(54) ORAL SOLID PREPARATION COMPRISING ARIPIPRAZOLE AND METHOD FOR PRODUCING ORAL SOLID PREPARATION COMPRISING ARIPIPRAZOLE

(71) Applicant: OTSUKA PHARMACEUTICAL CO., LTD., Tokyo (JP)

(72) Inventors: Haruka Yoshida, Osaka (JP); Toshiaki Taniguchi, Osaka (JP); Tadashi Mukai, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/264,693

(22) Filed: Apr. 29, 2014

(65) Prior Publication Data

US 2014/0322334 A1     Oct. 30, 2014

(30) Foreign Application Priority Data

Apr. 30, 2013 (JP) ................ 2013-095725

(51) Int. Cl.
C07D 215/227 (2006.01)
C07D 401/12 (2006.01)

(52) U.S. Cl.
CPC ................. *C07D 215/227* (2013.01)

(58) Field of Classification Search
CPC ............... C07D 215/227; C07D 401/12
See application file for complete search history.

(56) References Cited

U.S. PATENT DOCUMENTS

| | | | |
|---|---|---|---|
| 5,006,528 | A | 4/1991 | Oshiro et al. |
| 7,507,823 | B2 | 3/2009 | Worthen et al. |
| 7,807,680 | B2 * | 10/2010 | Kostanski et al. ....... 514/253.07 |
| 2004/0058935 | A1 * | 3/2004 | Bando et al. ............ 514/253.07 |
| 2005/0148597 | A1 | 7/2005 | Kostanski et al. |
| 2007/0213343 | A1 * | 9/2007 | Bando et al. ............ 514/253.07 |
| 2007/0272777 | A1 | 11/2007 | Samburski et al. |
| 2012/0322753 | A1 | 12/2012 | Zheng et al. |

FOREIGN PATENT DOCUMENTS

| | | |
|---|---|---|
| CN | 103172563 | 6/2013 |
| GB | 2505860 A | 12/2014 |
| JP | 02-191256 | 7/1990 |
| JP | 2608788 | 2/1997 |
| JP | 3760264 | 1/2006 |
| JP | 2007-0501236 | 1/2007 |
| JP | 2007-509153 | 4/2007 |
| JP | 2008-531737 | 8/2008 |
| JP | 2008-531738 | 8/2008 |
| JP | 2009-508859 | 3/2009 |
| JP | 4836797 | 10/2011 |
| JP | 4879349 | 12/2011 |
| WO | WO 03/026659 | 4/2003 |
| WO | WO03026659 | * 3/2004 ......... C07D 215/227 |
| WO | WO 2005/016262 | 2/2005 |
| WO | WO 2005/041937 | 5/2005 |
| WO | WO 2005/041970 | 5/2005 |
| WO | WO 2006/097344 | 9/2006 |
| WO | WO 2007/035348 | 3/2007 |
| WO | WO 2007/081366 | 7/2007 |
| WO | WO 2007/081367 | 7/2007 |
| WO | WO 2008/020820 | 2/2008 |
| WO | WO 2009/017250 | 2/2009 |
| WO | WO 2013/000391 A1 | 1/2013 |

OTHER PUBLICATIONS

Aoki et al.; "Study on Crystal Transformation of Aripiprazol", The Fourth Japan-Korea Symposium on Separation Technology, pp. 22, 937-940, (1996).
Yoshida et al.; "Oral Solid Preparation Comprising Aripiprazole and Method for Producing Oral Solid Preparation Comprising Aripiprazole", U.S. Appl. No. 14/265,883, filed Apr. 30, 2014.
International Search Report dated Sep. 12, 2014 for PCT/JP2014/061643.

* cited by examiner

*Primary Examiner* — Ernst V Arnold
(74) *Attorney, Agent, or Firm* — Finnegan, Henderson, Farabow, Garrett & Dunner, L.L.P.

(57) ABSTRACT

[Object] An object of the present invention is to provide an oral solid preparation that can be produced in a simpler manner than conventional methods, that exhibits high bioavailability and high dissolubility even in persons having low stomach acid, and that can also ensure dissolubility after being allowed to stand for a certain period of time. Another object is to provide a simple method for producing the oral solid preparation.
[Means for Achieving the Object] The present invention relates to an oral solid preparation comprising, as an active ingredient, a finely milled crystal obtained by milling an aripiprazole hydrate crystal, and a pharmaceutically acceptable carrier, the finely milled crystal having a mean particle size of 15 μm or less; and a method for producing an oral solid preparation comprising the steps of (1) milling an aripiprazole hydrate crystal into a finely milled crystal having a mean particle size of 15 μm or less, and (2) mixing the obtained finely milled crystal with a pharmaceutically acceptable carrier.

4 Claims, No Drawings

ORAL SOLID PREPARATION COMPRISING ARIPIPRAZOLE AND METHOD FOR PRODUCING ORAL SOLID PREPARATION COMPRISING ARIPIPRAZOLE

TECHNICAL FIELD

The present invention relates to an oral solid preparation comprising aripiprazole hydrate as an active ingredient, and a method for producing an oral solid preparation comprising aripiprazole hydrate as an active ingredient.

BACKGROUND ART

Aripiprazole, i.e., 7-{4-[4-(2,3-dichlorophenyl)-1-piperazinyl]butoxy}-3,4-dihydrocarbostyril or 7-{4-[4-(2,3-dichlorophenyl)-1-piperazinyl]butoxy}-3,4-dihydro-2(1H)-quinolinone, is known as an atypical antipsychotic that is useful for the treatment of schizophrenia, and aripiprazole anhydrous crystals are also known (Patent Document 1: JP1990-191256A and Non-patent Document 1: Proceedings of the Fourth Japan-Korea Joint Symposium on Separation Technology).

The aripiprazole anhydrous crystals have high hygroscopicity, and are therefore problematic in various ways (paragraph [0006] of Patent Document 2). One such problem is that, due to their high hygroscopicity, aripiprazole anhydrous crystals are prone to hydration. Furthermore, compared to anhydrous crystals, hydrated crystals are low in bioavailability and dissolubility. In particular, hydrated crystals exhibit low bioavailability and dissolubility in people with low stomach acid. A high proportion of Asian persons have low stomach acid. In Japanese, who are of Asian ethnicity, 25% of people 60 years of age or older are said to have low stomach acid.

There are also other problems caused by high hygroscopicity. For example, Patent Document 2 describes, as problems, the variation in the amount of aripiprazole hydrate versus anhydrous aripiprazole from batch to batch; reduced industrial production efficiency due to adhesion to a manufacturing apparatus during milling of the anhydrous; increased packaging cost due to concerns regarding moisture absorption during storage and handling; poor storage stability resulting from reduction of packaging cost; etc. (paragraph [0006] of Patent Document 2).

The aripiprazole anhydrous crystals disclosed in Patent Document 1 and Non-patent Document (NPL) 1 have problematically high hygroscopicity; however, such aripiprazole anhydrous crystals exhibit high bioavailability in persons having low stomach acid, and also have high dissolubility. Therefore, various research and analysis has been conducted on low hygroscopic aripiprazole anhydrous crystals.

As a result of such research and analysis, a novel low hygroscopic aripiprazole anhydrous crystal B that is resistant to hydration was successfully obtained from a novel aripiprazole hydrate A (Patent Document 2).

The low hygroscopic aripiprazole anhydrous crystal B can solve the above-mentioned various problems.

Patent Document 2 discloses that the novel aripiprazole anhydrous crystal B is produced by a method comprising milling a known aripiprazole hydrate (preferably monohydrate) to form a novel aripiprazole hydrate A, and heating the hydrate A to form a novel aripiprazole anhydrous crystal B.

PRIOR ART DOCUMENTS

Patent Documents

[Patent Document 1] JP1990-191256A (Japanese Patent No. 2608788)
[Patent Document 2] Japanese Patent No. 3760264

Non-Patent Document

[Non-patent Document 1] Satoshi Aoki et al., "Study on Crystal Transformation of Aripiprazole," Proceedings of the Fourth Japan-Korea Joint Symposium on Separation Technique (held on Oct. 6 to 8, 1996), pages 937 to 940 (issued in Japan)

SUMMARY OF INVENTION

Problem to be Solved by the Invention

However, the production process disclosed in the above Patent Document 2 comprises many production steps. If an oral solid preparation that exhibits high bioavailability and dissolubility in persons having low stomach acid can be produced in a simple manner, time and cost can be reduced.

Accordingly, an object of the present invention is to provide an oral solid preparation that can be produced in a manner simpler than conventional methods, that exhibits high bioavailability and high dissolubility even in persons having low stomach acid, and that can also ensure dissolubility after being allowed to stand for a certain period of time.

Another object of the present invention is to provide a simple method for producing an oral solid preparation that has high bioavailability and high dissolubility, and that can also ensure dissolubility after being allowed to stand for a certain period of time.

Means for Solving the Problem

As a result of extensive research, the present inventors achieved the above objects by attempting the use of an aripiprazole hydrate crystal, which has low bioavailability and low dissolubility, and which had been considered inapplicable to medicine by persons skilled in the art.

More specifically, the present invention uses a finely milled crystal obtained by simply milling an aripiprazole hydrate crystal to a mean particle size in a specific range, thereby providing an oral solid preparation that has high bioavailability and high dissolubility equivalent to those of an oral solid preparation comprising aripiprazole anhydrous crystal B, and that can also ensure dissolubility after being allowed to stand for a certain period of time.

Further, the present invention can provide a simple production method in which a finely milled crystal obtained by simply milling an aripiprazole hydrate crystal is directly used for the production of an oral solid preparation. For example, unlike the production process disclosed in Patent Document 2, the step of heating aripiprazole hydrate A for drying can be omitted.

The present invention provides oral solid preparations according to items 1 to 7, and methods for producing the oral solid preparations.

Item 1. An oral solid preparation comprising, as an active ingredient, a finely milled crystal obtained by milling an aripiprazole hydrate crystal, and a pharmaceutically acceptable carrier, the finely milled crystal having a mean particle size of 15 μm or less.

Item 2. The oral solid preparation according to item 1, wherein the finely milled crystal has a mean particle size of 14 μm or less.

Item 3. The oral solid preparation according to item 1, wherein the finely milled crystal has a mean particle size of 10 μm or less.

Item 4. The oral solid preparation according to item 1, wherein the finely milled crystal has a mean particle size of 5 μm or less.

Item 5. The oral solid preparation according to any one of items 1 to 4, wherein the finely milled crystal has a mean particle size of 1 μm or more.

Item 6. A method for producing an oral solid preparation comprising the steps of
(1) milling an aripiprazole hydrate crystal into a finely milled crystal having a mean particle size of 15 μm or less; and
(2) mixing the obtained finely milled crystal with a pharmaceutically acceptable carrier.

Item 7. The method for producing an oral solid preparation according to item 6, wherein the oral solid preparation is a tablet, and the method further comprises the step of (3) compressing the mixture obtained in step (2) into tablets.

Effect of the Invention

The present invention can provide an oral solid preparation that can be produced in a simpler manner than conventional methods, that exhibits high bioavailability and high dissolubility even in people having low stomach acid, and that can also ensure dissolubility after being allowed to stand for a certain period of time.

The present invention can further provide a simple method for producing an oral solid preparation that has high bioavailability and high dissolubility, and that can also ensure dissolubility after being allowed to stand for a certain period of time.

According to the present invention, the mean particle size of the particles of the aripiprazole hydrate crystal as an active ingredient is set to a specific low range. This enables the production of an oral solid preparation that has high dissolubility without being affected by the external environment (e.g., external humidity), and whose dissolubility after being allowed to stand for a certain period of time is also not impaired.

Further, the oral solid preparation of the present invention does not require the use of an aluminum pouch when packing the pharmaceutical in a blister pack (a FTP film), or a desiccant when sealing the pharmaceutical in a bottle.

Additionally, when using the method for producing the oral solid preparation of the present invention, the oral solid preparation obtained by the method has high dissolubility without being affected by hygroscopicity of aripiprazole as an active ingredient, and dissolubility of the preparation in the form of a tablet is also not impaired even after being allowed to stand for a certain period of time. Therefore, for example, when the preparation is formed into tablets, usable methods are not only a wet granule compression method or like production methods that comprise the steps of first preparing granules having a controlled water content, and then drying to reduce the water content of the granules; tablets can also be easily produced by other compression methods, such as a direct compression method or a dry granule compression method.

MODE FOR CARRYING OUT THE INVENTION

The expression "comprising" used herein includes the concepts of "comprising," "essentially consisting of," and "consisting of."

1. Oral Solid Preparation

The oral solid preparation of the present invention comprises, as an active ingredient, an aripiprazole hydrate crystal having a mean particle size of 15 μm or less, and a pharmaceutically acceptable carrier.

The aripiprazole hydrate crystals that can be used in the present invention are not particularly limited, and any crystals may be used.

Examples of aripiprazole hydrate crystals include the hydrate crystals disclosed in Reference Example 3 and Example 1 of Japanese Patent No. 3760264.

Compared to aripiprazole anhydrous crystals, aripiprazole hydrate crystals generally exhibit lower dissolubility in a dissolution test for oral solid preparations, and their dissolubility tends to decrease with the passage of time. However, the present invention suppresses the decrease in dissolubility by setting the particle diameter of aripiprazole hydrate crystals to a specific mean particle size.

Another excellent effect achieved by the present invention is that dissolubility is ensured, even when the preparation formed into tablets is allowed to stand for a certain period of time.

The aripiprazole hydrate crystals that can be used in the present invention are not particularly limited. Specific examples thereof include crystalline forms disclosed in Patent Document 2, specifically, aripiprazole hydrate A, and aripiprazole Type III disclosed in Non-patent Document 1. These crystalline forms can be prepared by the methods disclosed in Patent Document 2 and Non-patent Document 1.

The mean particle size of aripiprazole hydrate crystals is about 15 μm or less, preferably about 14 μm or less, more preferably about 10 μm or less, and even more preferably about 5 μm or less. Setting the mean particle size of aripiprazole hydrate crystals to about 15 μm or less can impart high dissolubility to the obtained oral solid preparation, and ensure dissolubility after being allowed to stand for a certain period of time.

Setting the mean particle size to the above-mentioned specific range can achieve a dissolution rate of about 60% or more at pH 5 after 60 minutes (the dissolution rate that can maintain the maximum blood concentration ($C_{max}$)) in dissolution tests performed immediately after the production of the oral solid preparation, and after lapse of time.

The mean particle size of aripiprazole hydrate crystals is not particularly limited. However, the mean particle size is preferably about 1 μm or more, more preferably about 2 μm or more, and most preferably about 2.5 μm or more from the viewpoint of preventing an increase of the mean particle size due to reaggregation, reducing costs while not requiring excessive time to mill aripiprazole hydrate crystals, and facilitating handling. In particular, setting the mean particle size of aripiprazole hydrate crystals to 2 μm or more, more preferably about 2.5 μm or more, is preferable because it prevents dissolubility variation of aripiprazole hydrous crystals as an active ingredient, and can stably provide an oral solid preparation with excellent dissolubility.

More specifically, the aripiprazole hydrate crystals preferably have a mean particle size of about 1 to 15 μm (particularly about 2 to 15 μm, and more particularly about 2.5 to 15 μm), more preferably about 1 to 14 μm (particularly about 2 to 14 μm, and more particularly about 2.5 to 14 μm), even more preferably about 1 to 10 μm (particularly about 2 to 10 μm, and more particularly about 2.5 to 10 μm, and still even more preferably about 1 to 5 μm (particularly about 2 to 5 μm, and more particularly about 2.5 to 5 μm).

The term "mean particle size" refers to volume mean diameter as calculated from the particle size distribution measured by a laser scattering particle size distribution analyzer.

The particle size ratio of the specific particle size of particles can be calculated from particle size distribution measured by a laser scattering particle size distribution analyzer.

The mean particle size measurement by the above method can also be performed using a light microscope. The measurement can be performed in accordance with the method described in the Japanese Pharmacopoeia (for example, B. General Tests, 3.04 Particle Size Determination, 1. First Optical Microscopy, described in the Handbook of the Japanese Pharmacopoeia, 16th Edition, Health, Labor and Welfare Ministry, Notification 65 (Mar. 24, 2011)). The mean particle size measured according to the method described in the Japanese Pharmacopoeia may be, for example, in the range of 3 to 20 µm.

The oral solid preparation preferably comprises an aripiprazole hydrate crystal in an amount of about 0.5 to 80 wt. %, and more preferably about 1 to 70 wt. %.

Examples of pharmaceutically acceptable carriers in the oral solid preparation of the present invention include diluents and excipients generally used in pharmaceuticals, such as fillers, extenders, binders, humectants, disintegrators, surfactants, and lubricants.

The pharmaceutical composition of the present invention may be in the form of a general pharmaceutical preparation. Examples of such forms include tablets, flash-melt tablets, pills, powders, granules, capsules, and the like.

When the preparation is formed into tablets, a wide variety of carriers conventionally known in this field can be used. Examples of such carriers include excipients such as lactose, sucrose, sodium chloride, glucose, urea, starch, xylitol, mannitol, erythritol, sorbitol, calcium carbonate, kaolin, crystalline cellulose, and silicic acid; binders such as water, ethanol, propanol, simple syrup, glucose solution, starch solution, gelatin solution, carboxymethyl cellulose, shellac, methylcellulose, potassium phosphate, and polyvinylpyrrolidones; disintegrators such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, and lactose; disintegration inhibitors such as sucrose, stearin, cacao butter, and hydrogenated oils; absorption enhancers such as quaternary ammonium base and sodium lauryl sulfate; humectants such as glycerol and starch; adsorbents such as starch, lactose, kaolin, bentonite, and colloidal silica; and lubricants such as purified talc, stearate, boric acid powder, and polyethylene glycol. Tablets can also be formed as tablets with ordinary coatings, if necessary. Examples of such tables include sugar-coated tablets, gelatin-coated tablets, enteric-coated tablets, film-coated tablets, double-layer tablets, and multilayer tablets.

When the preparation is formed into pills, a wide variety of carriers conventionally known in this field can be used Examples of usable carriers include excipients such as glucose, lactose, starch, cacao butter, hydrogenated vegetable oil, kaolin, and talc; binders such as powdered gum arabic, powdered tragacanth, gelatin, and ethanol; disintegrators such as laminaran and agar; and the like.

Capsules are prepared according to ordinary methods by mixing an aripiprazole hydrate crystal with one or more of various carriers as exemplified above, and packing the mixture in hard gelatin capsules, soft capsules, hydroxypropylmethyl cellulose capsules (HPMC capsules), or the like.

If necessary, colorants, preservatives, perfumes, flavorings, sweeteners, and the like, as well as other drugs may be incorporated into the pharmaceutical composition.

When the solid oral preparation is formed into granules, a liquid (typically, water or an aqueous solution containing a binder) is added to a mixed powder of granulating ingredients comprising an aripiprazole hydrate crystal and a carrier. As the carrier, various carriers known in this field can be used. Examples of such carriers include excipients, disintegrators, disintegration inhibitors, humectants, absorption enhancers, adsorbents, lubricants, colorants, and the like. Specific examples thereof include those mentioned above.

The oral solid preparation of the present invention may have any dissolution rate that is about 60% or more at pH 5 after 60 minutes as measured by a dissolution test method. When the dissolution rate at pH 5 after 60 minutes is about 60% or more, the active ingredient in the oral solid preparation administered can be sufficiently absorbed into the body, and the maximum blood concentration ($C_{max}$) can be maintained. Therefore, a dissolution rate of about 60% or more is preferable.

The dissolution test method is in accordance with the dissolution test method (paddle method) in the Japanese Pharmacopoeia, Sixteenth Edition, and is a method as described below.

One tablet of an oral solid preparation is added to 500 ml of acetate buffer (pH 5.0), which is used as a test liquid, thereby obtaining a test solution. Using the test solution, a dissolution test is performed at a paddle speed of 75 rpm in accordance with the method 2 (paddle method) for dissolution test. As the acetate buffer, a solution prepared by adding water to 1.97 g of acetic acid and 9.15 g of sodium acetate trihydrate to make 1000 ml of solution is used.

A standard solution is prepared in the following manner. 0.05 g of a standard sample of aripiprazole is weighed accurately, and ethanol (95%) is added to make exactly 50 ml of solution. Then, 6 ml of this solution is weighed accurately, and the test liquid is added to make exactly 1000 ml of solution.

The test solutions and the standard solution are subjected to filtration using a filter having a pore size of 10 or 20 µm. Each of the filtrates is introduced to a spectrophotometer equipped with a flow cell (cell length: 10 mm), and tested by UV visible absorbance spectroscopy. The differences between the absorbance of each solution at a wavelength of 249 nm and the absorbance thereof at a wavelength of 325 nm, which are At10, At20, At30, At45, At60, and As, are determined. At10, At20, At30, At45, and At60 indicate differences between the absorbances of each test solution at 10, 20, 30, 45, and 60 minutes after the beginning of the dissolution test, respectively. As indicates a difference between the absorbances of the standard solution.

The dissolution rate (%) relative to the indicated amount of aripiprazole is determined by the following formula:

Dissolution Rate (%) relative to the indicated amount of aripiprazole=Amount of the aripiprazole standard product (mg)×At×As×2

In the Formula. As indicates the difference between the absorbances of the standard solution, and At indicates At10, At20, At30, At45, or At60.

More specifically, the measurement of the dissolution rate by the above dissolution test method can be performed by the method shown in Test Example 1 of the Examples below.

The method for administering the oral solid preparation of the present invention is not particularly limited. The preparation can be orally administered by a method suitable for the patient's age, sex, and other conditions (e.g., severity of disease).

The dosage of the oral solid preparation of the present invention can be suitably selected according to the dose regimen, the patient's age, sex, and other conditions (e.g., severity of disease), etc. Generally, the preparation is administered in an amount such that the amount of aripiprazole, which is an active ingredient, is about 0.1 to 10 mg per kg of body weight per day. The amount of aripiprazole per tablet of the oral solid preparation is in the range of about 1 to 100 mg, and preferably about 1 to 30 mg.

The oral solid preparation of the present invention is effective in the prevention and treatment of schizophrenia, including intractable (drug-resistant, chronic) schizophrenia with cognitive impairment and intractable (drug-resistant, chronic) schizophrenia without cognitive impairment; anxiety, including mild anxiety; mania, including acute mania such as bipolar disorder acute mania; bipolar disorder; depression, including bipolar disorder depression; autism. Down's syndrome, attention deficit hyperactivity disorder (ADHD), Alzheimer's disease, Parkinson's disease, and like neurodegenerative diseases; panic, obsessive compulsive disorder (OCD), sleep disorder, sexual dysfunction, alcohol and drug dependency, vomiting, motion sickness, obesity, migraine, cognitive impairment, and like central nervous system diseases; and major depression, behavioral and psychological symptoms of dementia (BPSD), Tourette's syndrome, bulimia nervosa, and chronic pain/fibromyalgia/chronic fatigue syndrome.

2. Method for Producing the Oral Solid Preparation

The method for producing an oral solid preparation of the present invention comprises the steps of (1) milling an aripiprazole hydrate crystal to obtain a finely milled crystal having a mean particle size of 15 µm or less, and (2) mixing the obtained finely milled crystal with a pharmaceutically acceptable carrier.

The finely milled crystal obtained by milling in step (1) can be directly subjected to the subsequent step (2). For example, without drying after milling, the finely milled crystal can be used to produce the oral solid preparation.

Examples of the aripiprazole hydrate crystal used in step (1) may be the same as the hydrate crystals mentioned above in "1. Oral solid preparation."

The method for milling the aripiprazole hydrate crystal in step (1) is not particularly limited, and may be wet milling or dry milling. Various milling methods and mills can be used. The milling step can be performed by suitably selecting or suitably combining the conditions, devices, and methods that can produce an aripiprazole hydrate crystal having a mean particle size within the specific range of the present invention. From the viewpoint of ease of operation, dry milling is preferable.

When the milling in step (1) is performed by a dry milling method, examples of usable mills include jet mills, ball mills (e.g., Dyno mills), other low-energy mills (e.g., roller mills), and high-energy mills. Examples of high-energy mills include Netzsch mills, DC mills, planetary mills, and the like.

In particular, when a jet mill is used as a mill, the mean particle size of the milled aripiprazole hydrate crystal can be set by two types of air pressure ("forcing pressure" for feeding the powder to the milling chamber, and "milling pressure" of air directly sent to the milling chamber) and the "feed rate of the powder." Generally, as the air pressure is set high and the feed rate of the powder is set low, milling strength increases and the particle size tends to be small.

When the milling in step (1) is performed by wet milling, usable mills include, for example, high-pressure homogenizers and bead mills.

Step (2) is a step of mixing the aripiprazole hydrate crystal milled in step (1), and a pharmaceutically acceptable carrier.

Examples of pharmaceutically acceptable carriers used in step (2) may be the same as those mentioned above in "1. Oral solid preparation."

The mixing method in step (2) is not particularly limited as long as the milled aripiprazole hydrate crystal can be mixed with pharmaceutically acceptable carriers, such as excipients, binders, disintegrators, disintegration inhibitors, absorption enhancers, humectants, and adsorbents.

The powder of the aripiprazole hydrate crystal and the powder of a pharmaceutically acceptable carrier may be mixed by dry granulation, or may be mixed by wet granulation and formed into granules.

For wet granulation, various methods such as a fluidized bed granulation method, kneading granulation method, extrusion granulation method, and rotating granulation method can be used.

For example, when using a fluidized bed granulation method, granulating ingredients comprising various carriers are mixed by supplied air; while the granulating ingredients are continuously allowed to flow, a liquid is sprayed thereover to form granules. When using a kneading granulation method, granulating ingredients comprising various carriers are mixed by stirring; while the granulating ingredients are continuously stirred, a liquid is added thereto to form granules.

After the granulation, the obtained granules are, if necessary, passed through a screen to make the granules a desired size. The granules thus obtained are subjected to a drying process.

A wide variety of known methods can be used as the drying method. Examples of usable driers include fluidized bed dryers, fan dryers, vacuum dryers, and the like. For example, when using a fluidized bed dryer, the drying procedure is conducted with an air flow of 0.5 $m^3$/min to 50 $m^3$/min, and a supplied air temperature of 70 to 100° C. for about 10 minutes to 1 hour.

The content of the aripiprazole hydrate crystal in the mixture obtained in step (2) is preferably set to the same range as mentioned above in "1. Oral solid preparation."

When the oral solid preparation is formed into tablets by the method for producing the oral solid preparation of the present invention, the method further comprises a step of compressing the mixture obtained in step (2) into tablets.

Further adding a lubricant to the mixture obtained in step (2) is preferable in view of inhibiting the adhesion of the raw powder to a tableting machine during compression tableting in the subsequent step (3).

Various compression methods can be used in the compression tableting of step (3). Examples of usable methods include a wet granule compression method, direct powder compression method, dry granule compression method, and the like. Obtaining tablets by a direct powder compression method (direct compression method) is preferable in view of simple production of tablets that does not involve a complicated step of first preparing granules as in a wet granule compression method or dry granule compression method. Generally, when an oral solid preparation containing aripiprazole as an active ingredient is obtained by a direct compression method, low dissolubility tends to result. In contrast, in the present invention, because aripiprazole hydrate crystals as an active ingredient has a mean particle size within a specific range, a desired oral solid preparation comprising aripiprazole hydrate crystals, whose dissolubility is not reduced even when produced by a direct compression method, can be obtained.

When the oral solid preparation obtained by the production method of the present invention is formed into tablets, the tablets may be in the form of bilayer tablets, multilayer tablets, etc.

As long as high dissolubility, which is the effect of the present invention, is not impaired, a step of further coating may be performed, if necessary. For example, sugar-coated tablets, gelatin-coated tablets, enteric-coated tablets, and film-coated tablets can be produced.

The oral solid preparation obtained by the production method of the present invention exhibits the above-mentioned dissolution rate as measured by the dissolution test method described in "1. Oral solid preparation."

EXAMPLES

The present invention is explained in detail below with reference to the Examples and Comparative Examples; however, the present invention is not limited thereto or thereby.

Aripiprazole hydrate crystals used in the Reference Examples and Examples shown below were prepared based on Japanese Patent Publication No. 3760264.

Reference Examples 1 to 3 and Reference Example 5

Finely Milled Powder of Aripiprazole Hydrate Crystal

A crystal of aripiprazole hydrate A prepared based on Example 1 of Japanese Patent Publication No 3760264 was introduced into a jet mill (compact jet mill (JOM-min)), and subjected to dry mill by suitably adjusting air pressures (forcing pressure and milling pressure) and a feed rate so that the desired mean particle size was obtained. Milling was completed in 15 minutes, and a finely milled powder of aripiprazole hydrate crystal was obtained. The conditions of milling were suitably adjusted to obtain a desired mean particle size.

Reference Example 4

Finely Milled Powder of Aripiprazole Hydrate Crystal

Synthesis Example

Synthesis of Crude Aripiprazole

A 1.7-fold volume of purified water, 2.0-fold mol of potassium carbonate (anhydrous), and a 7.5-fold volume of ethanol were added to 7-hydroxy-3,4-dihydro-2(1H)-quinolinone (7-HDC) (standard amount), and the mixture was stirred at 40° C. for about 0.5 hour. 1.1-fold mol of 4-chlorobutyl 2-nitrobenzene sulfonate (CBNBS) was added thereto and reacted at about 40° C. for about 5 hours. After the solvent was distilled off, a 25-fold volume or more of purified water was added to the residue, followed by washing while stirring at about 50° C. The crystal was separated and washed with purified water.

A 14-fold volume of purified water, 1.07-fold mol of potassium carbonate (anhydrous), and 1.0 mol of 1-(2,3-dichlorophenyl)piperazine monohydrochloride(2,3-DCPP) were added to the obtained wet crystal, and the mixture was reacted at 80° C. or more for about 4 hours. After cooling, the crystal was separated and washed with purified water. A 34-fold volume of ethyl acetate was added to the obtained wet crystal, and heated until solvent reflux to distill ethyl acetate and remove water. After cooling, ethyl acetate in an amount equivalent to the amount removed by distillation and 5 wt % of activated carbon were added thereto, and refluxed for 0.5 hour or more. The reaction mixture was hot-filtered to distill off a 20-fold volume of ethyl acetate, and then cooled. The crystal was separated, and dried at about 55° C. to obtain crude aripiprazole.

The resulting crude aripiprazole (aripiprazole anhydrous crystal) was added to water-containing ethanol (ethanol: 80%, water: 20%), and heated to a solvent reflux temperature to completely dissolve the crude aripiprazole. The solution was cooled to precipitate an aripiprazole hydrate crystal, and the aripiprazole hydrate crystal was precipitated and milled by a wet pulverization device. After the solvent was removed by filtration, drying (air-drying overnight at room temperature) was performed to obtain an aripiprazole hydrate fine crystal (a crystal of aripiprazole hydrate A). The particle size was adjusted by wet pulverization operation conditions (suspension temperature, rotation speed, shape of wings for pulverization, etc.) to prepare a crystal of aripiprazole hydrate A having a desired particle size.

The particle size of the resulting finely milled powder of aripiprazole hydrate crystal was measured using Dry Unit 2000, which was a laser diffraction scattering particle size distribution analyzer (Laser Micron Sizer (LMS-2000e)), and the mean particle size was calculated from the obtained measurement results. Table 1 shows the measurement results.

The measurement conditions using a laser diffraction scattering particle size distribution analyzer were as follows: Particle refractive index: 1.750, imaginary part: 0.1, and dispersive pressure: 0.15 MPa.

Example 1

Tablet Containing Finely Milled Powder of Aripiprazole Hydrate Crystal (3 mg Per Tablet)

The finely milled powder of aripiprazole hydrate crystal (9.3 g) (3 mg/tab calculated in terms of aripiprazole anhydride mol) obtained in Reference Example 1, directly compressible lactose (207.0 g), corn starch (30.0 g), crystalline cellulose (30.0 g), and hydroxypropyl cellulose (6.0 g) were introduced into a high speed granulator (kneader mini NSK-150, produced by Gokyo Seisakusyo), and mixed for about 10 minutes by rotating blades at about 500 rpm.

The mixture obtained above was introduced into a drum container rotating-type mixer, then magnesium stearate (3.0 g) was added thereto and mixed. After mixing, the mixture was supplied to a tableting machine (high-speed rotary tablet press, VIRGO, produced by Kikusui Seisakusho Ltd.), and formed into tablets each having a weight of 95.1 mg using a die punch.

Examples 2 to 5

Tablet Containing Finely Milled Powder of Aripiprazole Hydrate Crystal (3 mg Per Tablet)

Tablets were obtained in the same manner as the method of Example 1, except that the finely milled powders obtained in Reference Examples 2 to 5 were used in place of the finely milled powder of aripiprazole hydrate crystal of Example 1.

Test Example 1

Tablet Stability Test

Each of the tablets of Examples 1 to 5 was allowed to stand under opening conditions 40° C./75% RH for one week, two weeks, or one month. The dissolution rate was measured according to the following method.

Dissolution Test Method

An acetic acid buffer (500 ml) with a pH of 5.0 was used as a test liquid, and one tablet was introduced into the test liquid, thereby obtaining a test solution. Using the resulting test solution, the test was performed at 75 rpm according to the second paddle method of the dissolution test method. The acetic acid buffer mentioned above was prepared as 1000 ml of the acetic acid buffer by dissolving acetic acid (1.97 g) and sodium acetate trihydrate (9.15 g) in water.

The dissolution liquids obtained 10, 20, 30, 45, and 60 minutes after the beginning of the test were respectively referred to as Test Solution T10, T20, T30, T45, and T60.

As a standard solution, an aripiprazole standard product (0.05 g) was accurately weighed, and ethanol (95%) was added and dissolved therein to obtain exactly 50 ml of a solution. 6 ml of the solution was accurately weighed, and a test liquid was added thereto to obtain exactly 1000 ml of solution.

Each of the test solutions and standard solution was passed through a filter having a pore size of 10 or 20 rm. Each of the filtrates was introduced into a spectrophotometer equipped with a flow cell (cell length of 10 mm), and a test was performed according to an UV visible absorption spectrometry. As and At10, At20, At30, At45, and At60, which were differences between the absorbance at a wavelength of 249 nm and the absorbance at a wavelength of 325 nm, were individually measured.

Each of Test Solutions T10, T20, T30, and T45 after measurement was placed back into individual test containers. The same operation was performed for the other five samples.

As a dissolution device, any test device that applies to the paddle method harmonized trilaterally by the US, EU, and JP can be used; however, the device shown below was used. In Examples 1 to 3 and 5, Model: NTR-6100, produced by Toyama Sangyo Co., Ltd. was used. In Example 4, Model: ITR-6200A, produced by Toyama Sangyo Co., Ltd. was used.

The dissolution rate (%) relative to the indicated amount of aripiprazole was determined by the following formula.

Dissolution Rate (%) relative to the indicated amount
of aripiprazole=Amount of the aripiprazole standard product (mg)×At×As×2

Herein, As indicates a difference between the absorbances of the standard solution, and At indicates At10, At20, At30, At45, or At60.

Table 1 shows the dissolution rate of each sample obtained 60 minutes after the start of the dissolution test. One sample was not allowed to stand (initial value), and the other samples were allowed to stand under the opening conditions of 40° C./75% RH for one week, two weeks, or one month.

TABLE 1

| Example | | Ex. 1 | Ex. 2 | Ex. 3 | Ex. 4 | Ex. 5 |
|---|---|---|---|---|---|---|
| Aripiprazole crystal form | | Finely milled powder of hydrate | | | | |
| Mean particle size of aripiprazole (μm) | | Ref. Ex. 1 2.6 | Ref. Ex. 2 4.8 | Ref. Ex. 3 4.9 | Ref. Ex. 4 9.5 | Ref. Ex. 5 13.7 |
| Dissolution rate (%) Initial value | 60 min | 93.9 | 88.1 | 93.2 | 79.91 | 63.5 |
| Dissolution rate (%) 40° C./75% RH Opening conditions Stored for one week | 60 min | 92.0 | 86.4 | 88.9 | 76.17 | 61.8 |
| Dissolution rate (%) 40° C./75% RH Opening conditions Stored for two weeks | 60 min | 93.0 | 86.1 | 91.1 | 76.49 | 61.4 |
| Dissolution rate (%) 40° C./75% RH Opening conditions Stored for one month | 60 min | 91.9 | 87.9 | 90.3 | 77.12 | 64.7 |

Comparative Examples 1 to 3

Tablet Containing Finely, Milled Powder of Aripiprazole Hydrate Crystal (3 mg Per Tablet)

In the same manner as Reference Example 4, finely milled powders of aripiprazole hydrate crystals were prepared by milling so that the mean particle sizes shown in Table 2 were obtained (Reference Examples 6 to 8). Using the finely milled powders of aripiprazole hydrate crystals obtained in Reference Examples 6 to 8, tablets were prepared in the same manner as Example 1. The dissolution rate of each of the obtained tablets of Comparative Examples 1 to 3 was measured in the same manner as the stability test (dissolution test) of Example 4. Table 2 shows the dissolution rate.

TABLE 2

| Example | | Comp. Ex. 1 | Comp. Ex. 2 | Comp. Ex. 3 |
|---|---|---|---|---|
| Aripiprazole crystal form | | Finely milled powder of hydrate | | |
| Mean particle size of aripiprazole (μm) | | Ref. Ex. 6 15.1 | Ref. Ex. 7 20.0 | Ref. Ex. 8 29.6 |
| Dissolution rate (%) Initial value | 60 min | 55.79 | 49.61 | 35.97 |
| Dissolution rate (%) 40° C./75% RH Opening conditions Stored for one week | 60 min | 53.92 | 49.99 | 34.21 |
| Dissolution rate (%) 40° C./75% RH Opening conditions Stored for two weeks | 60 min | 52.93 | 47.85 | 34.30 |
| Dissolution rate (%) 40° C./75% RH Opening conditions Stored for one month | 60 min | 53.41 | 47.17 | 35.09 |

Example

Tablets were prepared in the same manner as Example 1, except that components of the tablets were changed to the following. A stability test (including a dissolution test) was performed in the same manner as Example 4, Table 3 shows the results of the stability test (dissolution test).

The jet-milled a ipiprazole finely milled powder (hydrate crystal) (9.3 g) obtained in Reference Example 1, directly compressible lactose (114.0 g), crystalline cellulose (114.0 g), sodium carboxymethyl starch (21.0 g), carmellose calcium (21.0 g), and light anhydrous silicic acid (3.0 g) were introduced into a high speed granulator and mixed. Subsequently, magnesium stearate (3.0 g) was added thereto and mixed. The mixture was then supplied to a tableting machine, and formed into tablets using a die punch.

TABLE 3

| Example | | Example 6 |
|---|---|---|
| Finely milled, aripiprazole crystal (hydrate) | | Reference Example 1 |
| Mean particle size of aripiprazole (μm) | | 2.6 |
| Dissolution rate (%) Initial value | 60 min | 90.60 |
| Dissolution rate (%) 40° C./75% RH Opening conditions Stored for one week | 60 min | 90.11 |
| Dissolution rate (%) 40° C./75% RH Opening conditions Stored for two weeks | 60 min | 90.69 |
| Dissolution rate (%) 40° C./75% RH Opening conditions Stored for one month | 60 min | 88.61 |

The invention claimed is:

1. An oral solid preparation comprising, as an active ingredient, a finely milled crystal obtained by miffing an aripiprazole hydrate crystal, and a pharmaceutically acceptable carrier, the finely milled crystal having a mean particle size of 1 μm to less than 10 μm, and the oral solid preparation being in the form of a tablet, pill, granule, or capsule.

2. The oral solid preparation according to claim 1, wherein the finely milled crystal has a mean particle size of 1 to 5 μm.

3. A method for producing an oral solid preparation in the form of a tablet, pill, granule, or capsule, comprising the steps of:
   (1) milling an aripiprazole hydrate crystal into a finely milled crystal having a mean particle size of 1 μm to less than 10 μm; and
   (2) mixing the obtained finely milled crystal with a pharmaceutically acceptable carrier.

4. The method for producing an oral solid preparation according to claim 3, wherein the oral solid preparation is a tablet, and the method further comprises the step of (3) compressing the mixture obtained in step (2) into tablets.

* * * * *